United States Patent [19]
Burlingame

[11] Patent Number: 5,618,716
[45] Date of Patent: Apr. 8, 1997

[54] MATERIALS AND METHODS FOR BIOSYNTHESIS OF SERINE AND SERINE-RELATED PRODUCTS

[75] Inventor: Richard P. Burlingame, Manitowoc, Wis.

[73] Assignee: Wacker-Chemie GmbH, Munich, Germany

[21] Appl. No.: 244,491

[22] PCT Filed: Aug. 17, 1992

[86] PCT No.: PCT/EP92/01873

§ 371 Date: May 24, 1994

§ 102(e) Date: May 24, 1994

[87] PCT Pub. No.: WO93/12235

PCT Pub. Date: Jun. 24, 1993

[30] Foreign Application Priority Data

Dec. 12, 1991 [EP] European Pat. Off. ............ 91121385

[51] Int. Cl.$^6$ .......................... C12N 9/04; C12N 15/53
[52] U.S. Cl. .................. 435/106; 435/252.3; 435/320.1; 435/190; 435/325; 435/419; 435/108; 935/10; 935/14; 536/23.2
[58] Field of Search ...................... 935/10, 14; 435/190, 435/320.1, 252.3, 240.1, 240.2, 240.4; 536/23.2

[56] References Cited

U.S. PATENT DOCUMENTS

| | | | |
|---|---|---|---|
| 4,743,546 | 5/1988 | Backman et al. | 435/108 |
| 4,753,883 | 6/1988 | Backman et al. | 435/108 |

FOREIGN PATENT DOCUMENTS

| | | |
|---|---|---|
| 0190921 | 8/1986 | European Pat. Off. . |
| 0401735 | 12/1990 | European Pat. Off. . |
| 0418840 | 3/1991 | European Pat. Off. . |
| 0372962 | 7/1994 | European Pat. Off. . |

OTHER PUBLICATIONS

The Journal of Biological Chemistry, 1986 by the American Society of Biological Chemists, Inc., vol. 261, No. 26, pp. 12179–12183, Karen L. Tobey and Gregory A. Grant "The Nucleotide Sequence of the serA Gene of *Escherichia coli* and the Amino Acid Sequence of the Encoded Protein, D–3–Phosphoglycerate Dehydrogenase".

The Journal of Biological Chemistry, vol. 252, No. 8, pp. 1527–1551, 1977, Robert Dubrow and Lewis I. Pizer, "Transient Kinetic Studies on the Allosteric Transition of Phosphoglycerate Dehydrogenase".

Journal of Bacteriology, Jan. 1980, pp. 235–245, vol. 141, No. 1, John C. McKitrick and Lewis I. Pizer "Regulation of Phosphoglycerate Dehydrogenase Levels and Effect on Serine Synthesis in *Escherichia coli* K–12".

Journal of Bacteriology, Jun. 1971, pp. 972–982, vol. 106, No. 3, Tetsuya Tosa and Lewis I. Pizer, "Biochemical Bases for the Antimetabolite Action of L–Serine Hydroxamate".

T. M. Roberts et al., Gene 12 (1980), 123–127, Elsevier/ North–Holland Biomedical Press "A plasmid cloning vehicle allowing a positive selection for inserted fragments".

Experiments in Molecular Genetics, Cold Spring Harbor Press, pp. 201–205, Miller (1972), "Generalized Transduction; Use of P1 in Strain Construction".

Amundsen et al. (1986), Proc. Acad. Sci., U.S.A. 82, pp. 5558–5562, vol. 83 "The gene for an essential third subunit of exonuclease V".

Shevell et al. (1988), J. Bacteriol. 170, pp. 3294–3296, vol. 170, No. 7 "Construction of an *Escherichia coli* K–12 ada Deletion by Gene Replacement in a recD Strain Reveals a Second Methyltransferase That Repairs Alkylated DNA".

Experiments in Mol. Genetics, Cold Spring Harbor Lab., pp. 201–205 (1972), "Generalized Transduction; Use of P1 in Strain Construction".

Herrmann and Somerville (1983) (Amino Acids: Biosynthesis and Genetic Regulation).

Crueger and Crueger (1982) (Biotechnology: A Textbook of Industrial Microbiology).

Journal of Biological Chemistry, vol. 264, No. 5, 15 Feb. 1989, pp. 2645–2648, Baltimore, US, D.J. Schuller et al.: "Enhanced expression of the *Escherichia coli* serA gene in plasmid vector. Purification, crystallization, and preliminary X–ray data of D–3 phosphoglycerate dehydrogenase".

Bioscience Reports, vol. 1, No. 9, 1981, pp. 733–741, London, GB, G.A. Grant et al.: "D–3–phosphoglycerate dehydrogenase from *Escherichia coli*: Isolation by affinity chromatography and sequence comparison to other dehydrogenases".

Journal of Bacteriology, vol. 173, No. 5, Mar. 1991, p. 1571, Baltimore, US, K. O'Day et al.: "Physical location of bg1A and serA on the *Escherichia coli* K–12 chromosome".

Journal of Molecular Biology, vol. 186, No. 4, 20 Dec. 1985, pp. 707–713, London, GB, R. Cunin et al.: "Structure–function relationship in allosteric aspartate carbamoyltransferase from *Escherichia coli*. I. Primary structure of a pyrI gene encoding a modified regulatory subunit".

*Primary Examiner*—Keith D. Hendricks
*Attorney, Agent, or Firm*—Collard & Roe, P.C.

[57] ABSTRACT

Engineered DNA encoding 3-phosphoglycerate dehydrogenate (PGD) has reduced sensitivity to inhibition by serine in comparison to wild-type PGD. The DNA encodes PGD which has at least some level of enzymatic activity useful for biosynthesis, and which retains that activity at higher serine levels than does the (unmodified) wild-type PGD. The PGD has the amino acid sequence of this above-described engineered DNA. Expression vectors contain this engineered DNA and regulatory DNA positioned and oriented for expression of the engineered DNA in a host expression system. Cells contain these expression vectors, and a method for producing serine or a serine-derived product includes culturing such cells.

9 Claims, 7 Drawing Sheets

FIG. 2-1

```
          10                        30                         50
ATGGCAAAGGTATCGCTGGAGAGAAAGACAAGATTAAGTTTCTGCTGGTAGAAGGCGTGCAC
 MetAlaLysValSerLeuGluGluLysAspLysIleLysPheLeuLeuValGluGlyValHis 70                        90                       110
CAAAAGGCGCTGGAAAGCCTTCGTGCAGCTGGTTACACCAACATCGAATTTCACAAAGGC
 GlnLysAlaLeuGluSerLeuArgAlaAlaGlyTyrThrAsnIleGluPheHisLysGly 130                       150                       170
GCGCTGGATGATGAACAATTAAAAGAATCCATCCCCGATGCCCACTTCATCGGCCTGCGA
 AlaLeuAspAspGluGlnLeuLysGluSerIleArgAspAlaHisPheIleGlyLeuArg 190                       210                       230
TCCCGTACCCATCTCGACTGAAGACGTGATCAACGCCGCAGAAAAACTGGTCGCTATTGGC
 SerArgThrHisLeuThrGluAspValIleAsnAlaAlaGluLysLeuValAlaIleGly 250                        270                        290
TGTTTCTGTATCGGAACAAACCAGGTTGATCTGGATGCGGGGGGCAAAGCGCGGGATCCCG
 CysPheCysIleGlyThrAsnGlnValAspLeuAspAlaGlyAlaAlaLysArgGlyIlePro
```

FIG. 2-2

```
             310                          330                          350
GTATTTAACGCACCGTTCTCAAATACGCGCTCTGTTGCGGAGCTGGTGATTGGCGAACTG
 ValPheAsnAlaProPheSerAsnThrArgSerValAlaGluLeuValIleGlyGluLeu 370                          390                          410
CTGCTGCTATTGCGCGGGCGTGCCGGAAGCCAATGCTAAAGCGCACCGTGGCGTGTGGAAC
 LeuLeuLeuArgGlyValProGluAlaAsnAlaLysAlaHisArgGlyValTrpAsn 430                          450                          470
AAACTGGGCGCGGGTTCTTTTGAAGCGCGGGCAAAAAGCTGGGTATCATCGGCTACGGT
 LysLeuAlaAlaGlySerPheGluAlaArgGlyLysLysLeuGlyIleIleGlyTyrGly 490                          510                          530
CATATTGGTACGCAATTGGGCATTCTGGCTGAATCGCTGGGGAATGTATGTTTACTTTTAT
 HisIleGlyThrGlnLeuGlyIleLeuAlaGluSerLeuGlyMetTyrValTyrPheTyr 550                          570                          590
GATATTGAAAATAAACTGCCGCTGGGCAACGCCACTCAGGTACAGCATCTTTCTGACCTG
 AspIleGluAsnLysLeuProLeuGlyAsnAlaThrGlnValGlnHisLeuSerAspLeu
```

FIG. 2-3

```
                    610                630                650
CTGAATATGAGCGATGTGGTGAGTCTGCATGTACCAGAGAATCCGTCCACCAAAAATATG
LeuAsnMetSerAspValValSerLeuHisValProGluAsnProSerThrLysAsnMet 670                690                710
ATGGGGCGAAAGAAATTTCACTAATGAAGCCCGGCTCGCTGCTGATTAATGCTTCGCGC
MetGlyAlaLysGluIleSerLeuMetLysProGlySerLeuLeuIleAsnAlaSerArg 730                750                770
GGTACTGTGGTGGATATTCCGGCGCTGTGTGATGCGCTGGCGAGCAAACATCTGGCGGGG
GlyThrValValAspIleProAlaLeuCysAspAlaLeuAlaSerLysHisLeuAlaGly 790                810                830
GCGGCAATCGACGTATTCCCGACGGAACCGGGCGACCAATAGCGGATCCATTTACCTCCG
AlaAlaIleAspValPheProThrGluProAlaThrAsnSerAspProPheThrSerPro 850                870                890
CTGTGTGAATTCGACAACGTCCTTCTGACGCCACACATTGGCGGTTCGACTCAGGAAGCG
LeuCysGluPheAspAsnValLeuLeuThrProHisIleGlyGlySerThrGlnGluAla
```

FIG. 2-4

```
          910                   930                   950
CAGGAGAATATCGGCCTGGAAGTTGCGGGTAAATTGATCAAGTATTCTGACAATGGCTCA
GlnGluAsnIleGlyLeuGluValAlaGlyLysLeuIleLysTyrSerAspAsnGlySer 970                   990                  1010
ACGCTCTCTGCGGTGAACTTCCCGGAAGTCTCGCTGCCACTGCACGGTGGGGGTCGTCTG
ThrLeuSerAlaValAsnPheProGluValSerLeuProLeuHisGlyGlyGlyArgArgLeu 1030                  1050                  1070
ATGCACATCCACGAAAACCGTCCGGGCGTGCTAACTGCGCTGAACAAAATCTTCGCCGAG
MetHisIleHisGluAsnArgProGlyValLeuThrAlaLeuAsnLysIlePheAlaGlu 1090                  1110                  1130
CAGGGCGTCAACATCGCCGGCGCAATATCTGCAAACTTCCGCCCAGATGGGTTATGTGGTT
GlnGlyValAsnIleAlaAlaGlnTyrLeuGlnThrSerAlaGlnMetGlyTyrValVal 1150                  1170                  1190
ATTGATATTGAAGCCGACGAAGACGTTGCCGAAAAAGCGCTGCAGGCAATGAAAGCTATT
IleAspIleGluAlaAspGluAspValAlaGluLysAlaLeuGlnAlaMetLysAlaIle
```

FIG. 2-5

CCGGGTACCATTCGCGCCCGTCTGCTGTACTAA
ProGlyThrIleArgAlaArgLeuLeuTyrEnd
       1210                    1230

MATERIALS AND METHODS FOR BIOSYNTHESIS OF SERINE AND SERINE-RELATED PRODUCTS

BACKGROUND OF THE INVENTION

1. Field of the Invention

This invention relates to the general field of biosynthesis of serine and products related to serine, particularly tryptophan, and to methods and materials used in that biosynthesis.

2. The Prior Art

Serine is a primary intermediate in the biosynthesis of a wide variety of cellular metabolites including such economically important compounds as choline, glycine, cysteine and tryptophan. In addition, serine acts as a single carbon donor and is responsible for 60% to 75% of the total need of the cell for $C_1$ units through the production of 5,10-methylene-tetrahydrofolate from tetrahydrofolate. These $C_1$ units are used in a wide variety of biosynthetic pathways including the synthesis of methionine, inosine monophosphate, other purines and some pyrimidines (e.g., thymidine and hydroxymethyl cytidine).

The serine biosynthetic pathway shown in FIG. 1 is generally available to a wide variety of tissues and microorganisms. The first committed step in that pathway is the conversion of 3-phospho-D-glyceric acid (PGA) to 3-phosphohydroxypyruvic acid (PHA) by means of the enzyme 3-phosphoglycerate dehydrogenase (PGD). The gene encoding PGD has been cloned and sequenced, and the amino acid sequence of the PGD subunit has been deduced. Tobey and Grant, *J. Biol. Chem.*, 261:12179–12183 (1980).

In procaryotes (particularly bacteria) and microorganisms such as yeast, but not in higher eukaryotes, activity of wild-type PG is inhibited by cellular serine levels. This inhibition has been studied kinetically and reportedly proceeds in an allosteric manner. Tobey and Grant, *J. Biol. Chem.*, 261:12179–12183 (1986); Dubrow and Pizer, *J. Biol. Chem.*, 252:1527–1551 (1977); McKitrick and Pizer, *J. Bacteriol.*, 141:235–245 (1980).

Tosa and Pizer, *J. Bacteriol.*, 106:972–982 (1971), studied the effect of a normally toxic serine analog, L-serine hydroxamate, on an *E. coli* strain. Selection on a growth medium containing that analog yielded serine-resistant mutants. Some mutants were shown to have a modification in an enzyme unrelated to PGD, seryl-tRNA synthetase. Crude extract of one mutant showed PGD activity with reduced serine sensitivity (See, *J. Bacteriol.*, 106:972–982 [1971]; FIG. 5; Table 6; and see p. 973 bottom left col., p. 977 bottom left col.).

SUMMARY OF THE INVENTION

One aspect of the invention generally features DNA encoding 3-phosphoglycerate dehydrogenase (PGD) with reduced sensitivity to inhibition by serine in comparison to wild-type PGD, i.e., the DNA encodes PGD which has at least some level of enzymatic activity useful for biosynthesis, and which retains that activity at higher serine levels than does the (unmodified) wild-type PGD.

In preferred embodiments, the wild-type PGD is microbial or yeast PGD. Also preferably, the engineered DNA encodes PGD which comprises an alteration in the C-terminal 25% of wild-type PGD, preferably in the C-terminal 50 amino acids. For example, the engineered DNA may encode PGD comprising a deletion in part of all of the C-terminus. Also preferably, the engineered DNA encodes PGD having an insertion in the C-terminus (e.g., between VAL 363 and ASN 364, or between ALA 392 and GLN 394) in addition to the deletion described above, or as a separate alteration.

The present invention is also directed to: a) PGD having the amino acid sequence of the above-described engineered DNA; b) expression vectors comprising the engineered DNA and regulatory DNA positioned and oriented for expression of the engineered DNA in a host expression system; c) cells comprising such expression vectors; and d) methods for producing serine or a serine-derived product by culturing such cells. As to c) above, the cell preferably is deleted for wild-type serA.

Yet another embodiment generally features a cell engineered (e.g., it includes a recombinant genetic construction) to produce a PGD-encoding mRNA transcript with an altered 3' end, which transcript is translated by the cell to yield PGD with reduced sensitivity to inhibition by serine in comparison to wild-type PGD.

The present invention provides decontrol of an important biosynthetic control point, thereby enhancing production of numerous compounds downstream of that point, including, in particular, serine and serine-derived products such as tryptophan. Other cellular metabolites derived from serine (i.e., serine is a primary intermediate in their biosynthesis) include choline, glycine, cysteine and $C_1$-donor-dependent compounds such as methionine, inosine monophosphate, purines, and some pyrimidines (e.g., thymidine and hydroxymethyl cytosine).

BRIEF DESCRIPTION OF THE DRAWINGS

Other objects and features of the present invention will become apparent from the following detailed description considered in connection with the accompanying drawings, which disclose the embodiments of the present invention. It should be understood, however, that the drawings are designed for the purpose of illustration only and not as a definition of the limits of the invention.

In the drawings, wherein similar reference characters denote similar elements throughout the several views:

FIGS. 2(1)–2(5) show the sequence of the *E. coli* serA gene reported by Tobey and Grant (cited above) and the amino acid sequence deduced from the gene.

DETAILED DESCRIPTION OF THE PREFERRED EMBODIMENTS

Providing Serine-Insensitive PGD

Figure 1:
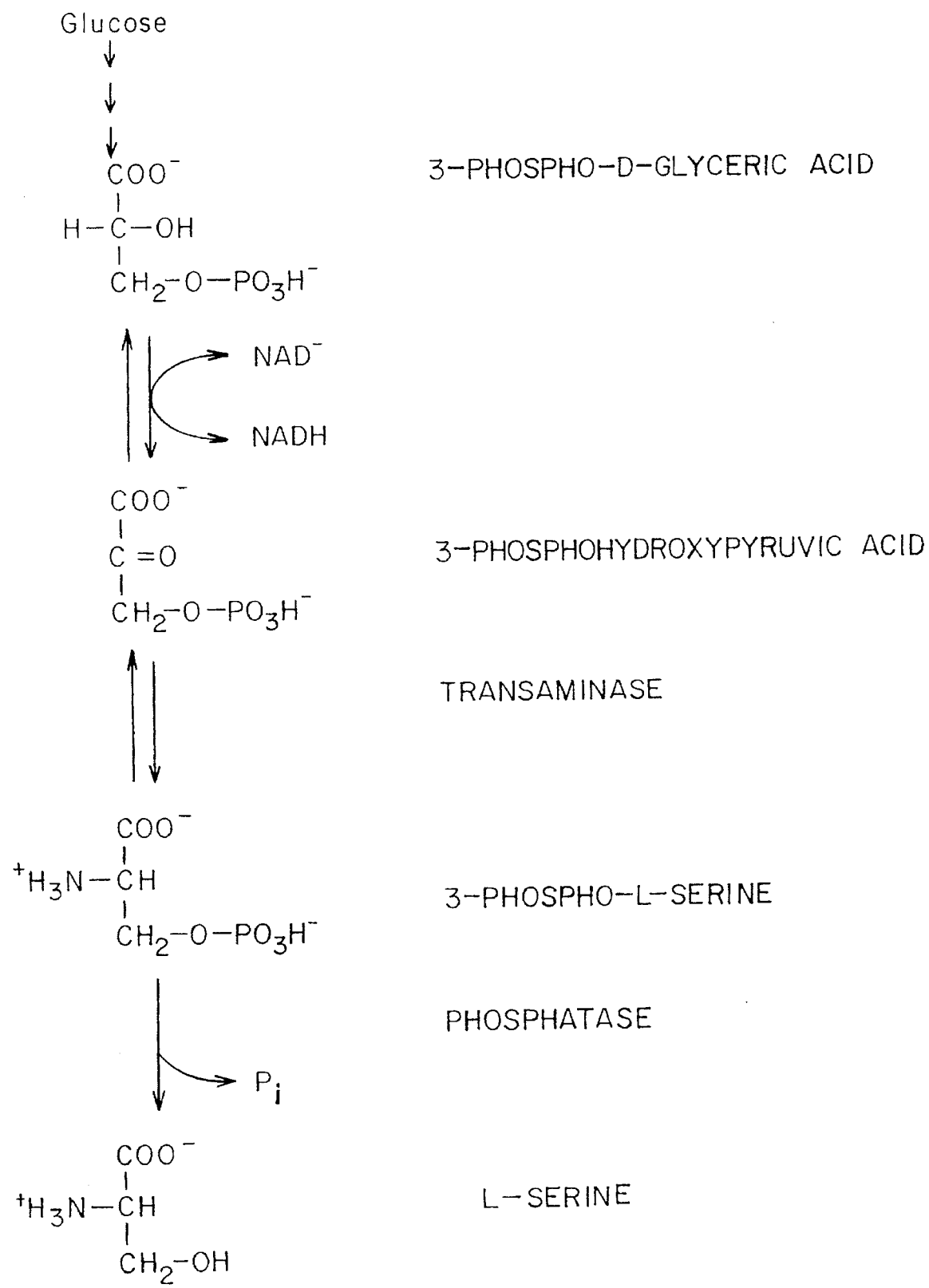
FIG. 1 shows the steps in the biosynthesis of L-serine from glucose.

1. Genetically Engineered Constructions.

The preferred embodiments of the invention feature biosynthesis of serine and serine-related products, e.g., products described above derived by biosynthesis from serine. A first step in biosynthesis of these compounds according to the invention is the provision of serine-insensitive PGD, as discussed below.

It has been determined that there is a specific serine feedback mediating domain in PGD, and that domain can be altered to reduce serine sensitivity while maintaining useful levels of PGD activity. FIG. 2 shows one particular PGD genetic and amino acid sequence (SEQ ID NO: 1) which can be used for reference in the following discussion. The sequence of FIG. 2 (SEQ ID NO: 1) includes 410 amino acids (including the initial Met which is cleaved from the mature protein). The domain of PGD that can reduce serine sensitivity, without destroying PGD activity, is within the C-terminal 25% of the molecule, most preferably the 50 C-terminal residues.

Examples of PGD modifications that fall within the invention are deletions of some or all of the C-terminal 42 amino acids, or insertions or substitutions within that region which reduce serine insensitivity while retaining useful PGD function. For example, insertion of amino acid residues between Val 363 and Asn 364 will increase the $K_i$ of the PGD over wild-type, while retaining PGD activity.

More dramatic increases in $K_i$ are accomplished by deleting some or all of the C-terminal amino acid residues. For example, deletion of the C-terminal residues GTIRARLLY and replacement with ASLD increases $K_i$ by several orders of magnitude, while retaining a useful level of PGD activity. Other insertions within the scope of the invention are insertions between Ala 392 and Gln 394.

Other useful modifications include deletions from the C-terminus in addition to the insertions and modifications discussed above.

Genes encoding serine-insensitive PGD described above can be constructed by genetic engineering techniques that involve altering the 3' end of the coding region coding for the C-terminal amino acids, and then transforming a host strain with a vehicle to express the altered PGD enzyme. Candidate altered enzymes are screened (as described below) for serine affinity ($K_i$) and for PGD activity by the methods generally discussed below.

2. Screening the Genetically Engineered Constructions.

In screening genetic constructions made by the above-described methods, the following assays of PGD activity and of serine sensitivity are used.

While not critical to the invention, the assay of PGD activity is generally necessary in order to establish the degree of serine sensitivity of the altered enzyme. As is well known in the art, enzyme activity is a function of the total number of enzyme molecules and the catalytic activity of each molecule. Thus, in comparing the catalytic activity of PGD feedback variants, steps must be taken to adequately control for the relative number of PGD molecules for samples in which relative catalytic activity is to be compared. There are a number of ways in which this may be accomplished. However, since it is difficult to adequately establish the level of gene expression in cells transformed with truncated serA genes (due to decreased viability), the most suitable way to compare PGD activity produced from various constructs and the wild type is to chromosomally integrate the altered serA gene containing standard regulatory elements in a single copy, followed by harvesting the transformants and determination of the relative catalytic activity as compared to PGD from wild type cells.

Any method suitable for the measurement of PGD activity may be employed. PGD activity may be measured through detection of either the forward or the reverse reaction by the method of John C. McKitrick and Lewis I. Pizer, *J. Bacteriol.*, 141:235–245 (1980).

The enzymatic assay described above is suitable for determination of serine sensitivity for any PGD enzyme, including those with chemically modified C-termini. The assay is performed in the presence of various levels of serine. The catalytic activity in the presence of serine is compared to catalytic activity in the absence of serine, and the $K_i$ calculated.

In most cases it will be preferred to reduce serine sensitivity without significantly altering PGD catalytic activity. In still other embodiments it may be desirable to reduce both the feedback sensitivity and the catalytic activity. The constructions having a C-terminal amino acid sequence of 3-phosphoglycerate dehydrogenases listed in TABLE 1 (described below) may be used.

TABLE 1

| | C-terminal Amino Acid Sequences of 3-phosphoglycerate dehydrogenases | | |
|---|---|---|---|
| serA | Sequence | ki/mM | Units |
| WT | (SEQ ID NO: 2) | <0.1 | .05 |
| 1455 | (SEQ ID NO: 3) | >100 | <.01 |
| 1459 | (SEQ ID NO: 4) | >100 | N/A |
| 1507 | (SEQ ID NO: 5) | >100 | N/A |
| 1508 | (SEQ ID NO: 6) | 3.8 | 0.5 |
| 1509 | (SEQ ID NO: 7) | >100 | N/A |
| 1510 | (SEQ ID NO: 8) | >100 | N/A |
| 1511 | (SEQ ID NO: 9) | >100 | N/A |
| 1512 | (SEQ ID NO: 10) | >100 | N/A |
| 1530 | (SEQ ID NO: 11) | >100 | N/A |
| 1531 | (SEQ ID NO: 12) | >100 | N/A |

Other constructions with modified 3' ends also fall within the scope of the present invention since it is a simple matter to prepare test constructs and transform cells according to the present invention and test for serine inhibition of PGD activity.

Any vector which leads to expression of a PGD protein lacking sensitivity to inhibition by serine pertains to the present invention. In general, however, in the absence of a sink for serine, high levels of expression of feedback free PGD should be avoided since the resulting high cytoplasmic levels of serine or serine-derived metabolites can be toxic to the cell. Thus, in general, for any construct coding for a feedback inhibited PGD with normal catalytic activity and expression levels similar to those from the native gene, transformation will likely lead to high levels of PGD expression and decreased cellular viability. The toxicity of high levels of serine produced may, in fact, select for mutants with decreased PGD expression. Thus, while transformation using multi-copy plasmids may be useful in initial screening of constructs with some embodiments, it is preferred to chromosomally integrate serA constructs in single copies into the genome. Additionally, chromosomal integration as described below facilitates activity measurement of the feedback deleted PGD. Thus, in most embodiments where strong catalytic activity is expected or desired, it is preferred to utilize vectors suitable for single copy chromosomal integration. Many such vectors and strategies for their use are known in the art. See, e.g., Backman, U.S. Ser. No. 07/091,837, filed Sep. 1, 1987, hereby incorporated by reference. Useful vectors and constructs can be made to allow for the successful transformation and expression of the enzyme in an appropriate host for producing the desired product. Means for accomplishing these ends are well known to those familiar with the art and are not central to the present invention. In addition to the altered PGD-encoding DNA, the expression vector will contain various other elements described below.

First, the coding sequences present on the vector will be accompanied by the appropriate regulatory elements necessary for the appropriate level of expression of the coding sequences, including promoters, ribosome binding sites, and termination sequences. In most cases, the native serA regulatory sequences will be the preferred source of the catalytically active part of the molecule, although it is recognized that many other regulatory sequences known to the art or yet to be discovered may be employed.

Second, it is preferred that sequences encoding selective markers and/or reporter genes, along with the appropriate regulatory elements, will also be present on the vector. The expression of such selective markers is useful in identifying transformants. Appropriate selective marker genes include those coding for ampicillin, tetracycline, and chloramphenicol.

Third, the desirability of an origin of replication on the plasmid vector depends largely on the desirability of maintaining the genes chromosomally or extrachromosomally. Those familiar with the art appreciate the various strategies by which the lack of an origin of replication can be exploited to promote integration into the chromosome. See, e.g., Backman et al, U.S. Pat. No. 4,743,546, hereby incorporated by reference.

Once the expression vector is constructed, a suitable host cell can be transformed with a vector containing a transcription unit coding for a serine insensitive PGD protein. In most cases, it is useful to employ cells for which the endogenous PGD protein is known to be inhibited by serine and in which the endogenous serA gene is deleted and replaced by the altered gene of the invention. Such cell systems are useful for the overproduction of serine-related metabolites. Cells known to contain serine sensitive proteins are prokaryotes and yeasts.

The following example illustrates, but does not limit, the invention.

EXAMPLE 1

Construction of serA Gene Alleles Encoding Feedback Resistant 3-phosphoglycerate Dehydrogenases The E. Coli K12 serA gene was isolated on a 6.4 Kb DNA fragment from a Sau3A partial digest cloned into the BclI site of pTR264. See, Backman et al., U.S. Ser. No. 07/285, 128, filed Dec. 16, 1988; and Roberts et al., Gene, 12:123 (1980). This plasmid was named pKB1302. A 3 Kb SalI to SphI fragment of pKB1302 DNA containing the serA gene was cloned into pUC19 to generated pKB1321. pKB1370 was generated by cloning a 3 Kb HindIII to SalI fragment containing the serA gene into pBR322.

Alleles of serA encoding feedback resistant 3-phosphoglycerate dehydrogenases were generated by inserting XbaI linkers at restriction sites in the 3' region of the serA gene. A partial digest of plasmid pKB1321 by HincII yielded blunt ends at position 1793, where insertion of linkers gave: a) pKB1459, encoding a truncated 3-phosphoglycerate dehydrogenase; b) pKB1507, encoding a truncated 3-phosphoglycerate dehydrogenase; and c) pKB1508 which encodes a 3-phosphoglycerate dehydrogenase with a four amino acid residue insert.

PstI digestion of pKB 1321 gives 3' overhang at position 1888. Blunt ends were generated by the action of the Klenow fragment of DNA polymerase I. Linkers were ligated into the blunt end fragments and the derived plasmids were pKB1509 which encodes a 3-phosphoglycerate dehydrogenase with a two-amino-acid insert and pKB1510 which encodes a truncated 3-phosphoglycerate dehydrogenase. A KpnI digest of pKB1370 was made blunt ended with Klenow fragment of DNA polymerase I and inserted linkers yielded plasmids encoding truncated 3-phosphoglycerate dehydrogenase, pKB1455 and pKB1512, or 3-phosphoglycerate dehydrogenase with a two amino acid residue insert, pKB1511. Deletion plasmids pKB1530 and pKB1531 were generated by inserting the 0.8 Kb BamHI to XbaI fragment from pKB1508 or the 0.9 Kb BamHI to XbaI fragment from pKB1509, respectively, into the 5.8 Kb BamHI to XbaI fragment of pKB1511.

The following TABLE 2 summarizes the various constructs made.

TABLE 2

| serA Allele | Plasmid | Restriction Site | Linker | Result |
| --- | --- | --- | --- | --- |
| Ser A 1455 | pKB 1370 | Kpn I | SEQ ID NO: 13 | Truncated |
| Ser A 1459 | pKB 1321 | Hind II | SEQ ID NO: 13 | Truncated |
| Ser A 1507 | pKB 1321 | Hind II | SEQ ID NO: 14 | Truncated |
| Ser A 1508 | pKB 1321 | Hind II | SEQ ID NO: 15 | Insert |
| Ser A 1509 | pKB 1321 | Pst I | SEQ ID NO: 16 | Insert |
| Ser A 1510 | pKB 1321 | Pst I | SEQ ID NO: 15 | Truncated |
| Ser A 1511 | pKB 1370 | Kpn I | SEQ ID NO: 17 | Insert |
| Ser A 1512 | pKB 1370 | Kpn I | SEQ ID NO: 18 | Truncated |
| Ser A 1530 | pKB 1511 + pKB 1508 | Hind II + Kpn I | | Deleted |
| Ser A 1531 | pKB 1511 + pKB 1509 | Pst I + Kpn I | | Deleted |

For all the constructs, the starting vector, the restriction site used, and the sequence of the inserted linker are indicated. The Ki values for serine are given in Table 1, as well as the relative catalytic activity for three of these constructs following chromosomal integration (described below). N/A indicates that the construction was not chromosomally integrated, and the activity level therefore was not standardized.

3. Chemical Modifications

Those skilled in the art will understand that deletions or modifications of the C-terminus of wild-type PGD can be accomplished enzymatically or chemically, e.g., by various carboxypeptidases, including carboxypeptidase Y or by lactoperoxidase mediated iodination.

4. Use of Antisense mRNA

Alternatively, it may be possible to reduce serine sensitivity in vivo through the generation of PGD-encoding transcripts truncated at the 3' end by means of the producing antisense mRNAs that include nucleotide sequences complementary to portions of the 3' coding region of native or transformed PGD coding sequences.

C. Production of Desired Compounds

Figure 3:
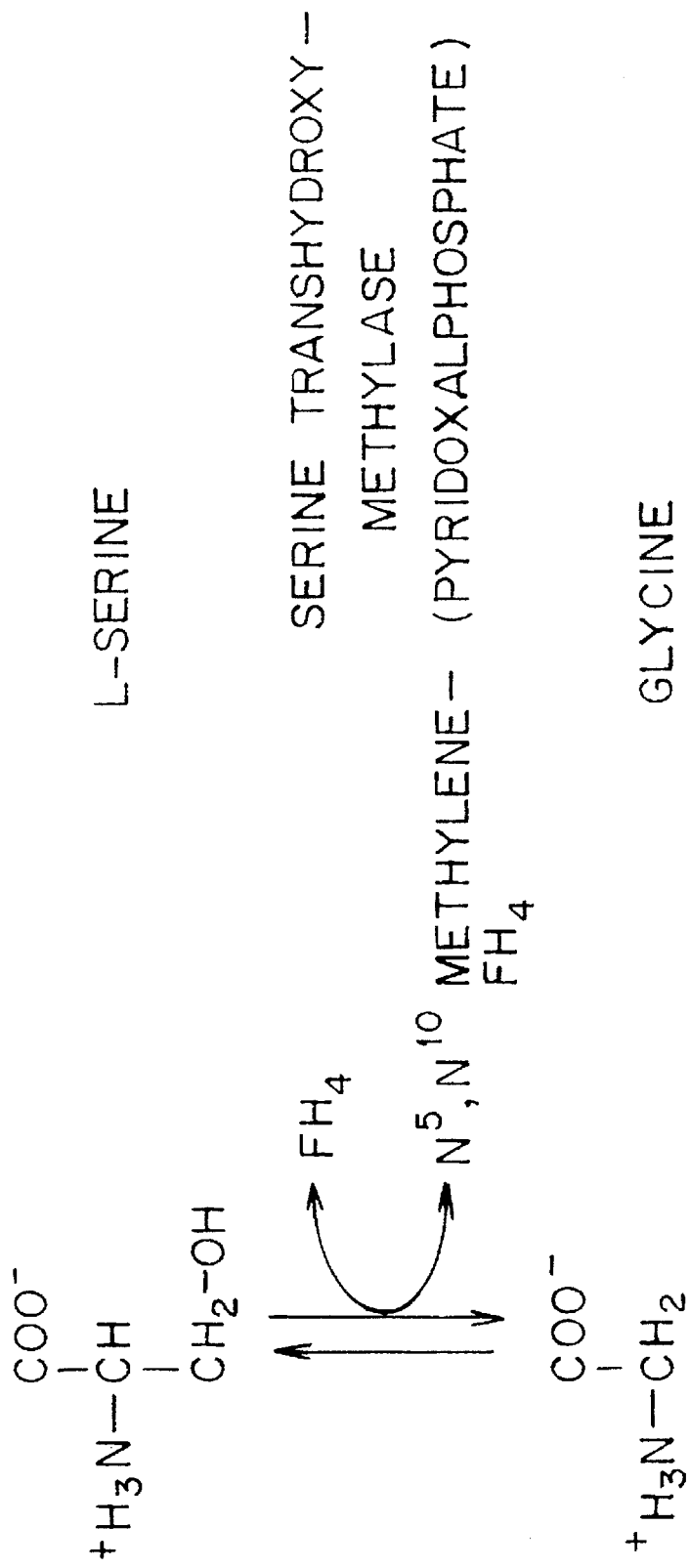
FIG. 3 depicts bioconversion of L-serine and tetrahydrofolate to glycine and $N^5,N^{10}$-methylene tetrahydrofolate.

As shown in FIG. 3, serine is an intermediate in the production of glycine. It is also an intermediate in the production of $N^5N^{10}$-methylenetetrahydrofolate which is generalized $C_1$ donor essential for synthesis of methionine, purines (including inosine) and some pyrimidines. Thus, the over-production of serine from phosphoglycerate may be useful in a wide range of bacterial production systems, including production systems for choline, glycine, cysteine, methionine, tryptophan, and al purines, including inosine monophosphate.

The following specific examples further illustrate the invention.

EXAMPLE 2

Host Strain Preparation

Sequences internal to a plasmid born serA gene were replaced with a kanamycin resistance gene. This plasmid was then used to inactivate the host strain serA gene by means of allele exchange, as follows.

The serA region of YMC9 (ATCC33920) was cloned from chromosomal DNA, partially digested with Sau 3AI, by complementation of PC1523 (argI61, argF58, serA27, purA54, thr-25, tonA49, relA1, spoT1), obtained from Coli Genetic Stock Center, Yale University, New Haven, Conn. A 3 kb fragment carrying the serA gene was subcloned into pUC19, giving rise to a plasmid called pKB1321. From this plasmid, a 3 kb SalI to HindIII fragment was recloned into pBR322, giving rise to plasmid pKB1370. The KpnI site at the 3' end of the serA gene was converted to BamHI with a linker and the BamHI fragment internal to the resulting serA was replaced with the BamHI fragment from pUC-4-KSAC (Pharmacia) containing the Tn903 kanamycin resistance gene. This new plasmid was designated pKB1429. A pBR322 derivative called pKB 701 (ATCC39772) (see U.S. Ser. No. 06/757,014, hereby incorporated by reference) was generated in which the MboI and TThIII 1 flanking the origin of replication were converted to KpnI sites. The SalI to EcoRI fragment containing serA::KanR from pKB1429 was cloned into pKB701, giving rise to pKB1438. pKB1438 was digested with KpnI to remove the ori region. The large fragment containing the ampicillin resistance coding region, as well as the serA::KanR, was circularized and used in a $CaCl_2$ transformation of YMC9. Following transformation, the host YMC9 cells were placed under selection on ampicillin. Under these conditions, ampicillin resistant clones develop by incorporation of the circular DNA through homologous recombination in the serA gene flanking regions. Growth of the ampicillin resistant isolate in the absence of ampicillin selection results in loss of the ampicillin resistance gene by homologous recombination of the repeated sequences of serA gene flanking regions. Such strains were identified by the loss of production of β-lactamase using AmpScreen (BRL) according to the manufacturer's directions. Duplicate streaking of single colonies on media in the presence and absence of serine revealed ampicillin sensitive clones requiring serine for growth on minimal medium and which were also resistant to kanamycin. One such isolate was named KB875.

EXAMPLE 3

Chromosomal Integration of Altered serA Sequences by Allele Exchange

The serA 1455 allele was introduced to the chromosome by a process analogous to that used for the introduction of serA::KanR as described in Example 2. Briefly, a fragment (SalI to HindIII) bearing the serA 1455 allele was cloned into pKB701. The plasmid origin was removed by KpnI digestion. The circularized DNA was used to transform to ampicillin resistance giving rise to a strain designated.

After non-selective growth, using Ampscreen and replica plating for kanamycin, KB904 (serA 1455) was isolated and shown to be sensitive to ampicillin and kanamycin KB904. The resulting serA 1455 allele can be transferred into production strains by P1 transduction. Miller, *Experiments in Mol. Genetics,* Cold Spring Harbor Press, pp. 201–205 (1972).

EXAMPLE 4

Chromosomal Integration of Altered serA Sequences by recD Dependent Gene Replacement.

Another approach was utilized to move the serA1508 allele on to the chromosome. The strain KB875 was made recD by P1 transduction from V220 (recD, argA:Tn10. Amundsen et al., *Proc. Acad. Sci., U.S.A.,* 82:5558–5562 [1986]) (DSM 6823). The gene for an essential third subunit of exonuclease V. to give JGP101. The plasmid pKB1508 was linearized and used to transform JGP101 to serine prototrophy essentially as described by Shevell et al., *J. Bacteriol.,* 170:3294–3296 (1988), to give JGP103. The serA1508 allele can then be moved to production strains by P1 transduction. Miller et al., *Experiments in Mol. Genetics,* Cold Spring Harbor Lab., pp. 201–205 (1972).

Harvesting of Overproduced Metabolites

For the overproduction of serine-related metabolites, cells can be prepared which produce PGD with reduced serine sensitivity, and grown in fermentors under the appropriate conditions, in most cases to stationary phase. The cells will then be harvested and lysed and the desired metabolite prepared according to standard biochemical procedures. Conditions, principles, and references for the growth of microbes, and the harvesting of specific metabolites, are provided by Crueger and Crueger, *Biotechnology: A Textbook of Industrial Biology* (1982) and Herrmann and Somerville, *Amino Acids: Biosynthesis and Genetic Regulation* (1983), incorporated herein by reference.

While several embodiments of the present invention have been shown and described, it is to be understood that many changes and modifications may be made thereunto without departing from the spirit and scope of the invention as defined in the appended claims.

---

I claim:

1. Engineered DNA encoding 3-phosphoglycerate dehydrogenase (PGD) from *E. Coli* with reduced sensitivity to inhibition by serine in comparison to wild-type PGD;
   said DNA encoding PGD from *E. Coli* comprising a C-terminal insertion into a wild-type PGD sequence;
   wherein said insertion is between VAL 363 and ASN 364 of wild-type PGD of (SEQ ID NO:1) or between ALA 392 and GLN 394 of wild-type PGD (SEQ ID NO:1).

2. An expression vector comprising
   the engineered DNA of claim 1 and regulatory DNA positioned and oriented for expressing said engineered DNA in a host expression system.

3. A cell comprising the engineered DNA of claim 1, and regulatory DNA positioned and oriented to express said engineered DNA in said cell.

4. The cell of claim 3, in which said cell is deleted for wild-type serA.

5. A method for producing a product selected from the group consisting of serine and a serine-derived product, comprising
   culturing a cell according to claim 3; and
   recovering said product.

6. The method of claim 5, in which said product is serine.

7. A 3-phosphoglycerate dehydrogenase having the amino acid sequence encoded by the engineered DNA of claim 1.

8. Engineered DNA encoding 3-phosphoglycerate dehydrogenase (PGD) from *E. coli* with reduced sensitivity to inhibition by serine in comparison to wild-type PGD;
   said DNA encodes PGD from *E. coli* having an amino acid sequence selected from the group consisting of the following
   (SEQ ID NO.: 3);
   (SEQ ID NO.: 4);
   (SEQ ID NO.: 5);
   (SEQ ID NO.: 6);
   (SEQ ID NO.: 7);
   (SEQ ID NO.: 8);
   (SEQ ID NO.: 9);
   (SEQ ID NO.: 10);
   (SEQ ID NO.: 11); and
   (SEQ ID NO.: 12)
   instead of deleted 52 C-terminal amino acids of the wild-type PGD of (SEQ ID NO.: 1).

9. A 3-phosphoglycerate dehydrogenase having the amino acid sequence encoded by the engineered DNA of claim 8.

* * * * *

SEQUENCE LISTING ( 1 ) GENERAL INFORMATION:

( i i i ) NUMBER OF SEQUENCES: 18

( 2 ) INFORMATION FOR SEQ ID NO:1:

( i ) SEQUENCE CHARACTERISTICS:
( A ) LENGTH: 1233 base pairs
( B ) TYPE: nucleic acid (C) STRANDEDNESS: double
(D) TOPOLOGY: linear (ii) MOLECULE TYPE: other DNA (xi) SEQUENCE DESCRIPTION: SEQ ID NO:1:

```
ATG GCA AAG GTA TCG CTG GAG AAA GAC AAG ATT AAG TTT CTG CTG GTA        48
Met Ala Lys Val Ser Leu Glu Lys Asp Lys Ile Lys Phe Leu Leu Val
 1               5                  10                  15

GAA GGC GTG CAC CAA AAG GCG CTG GAA AGC CTT CGT GCA GCT GGT TAC        96
Glu Gly Val His Gln Lys Ala Leu Glu Ser Leu Arg Ala Ala Gly Tyr
             20                  25                  30

ACC AAC ATC GAA TTT CAC AAA GGC GCG CTG GAT GAT GAA CAA TTA AAA       144
Thr Asn Ile Glu Phe His Lys Gly Ala Leu Asp Asp Glu Gln Leu Lys
         35                  40                  45

GAA TCC ATC CGC GAT GCC CAC TTC ATC GGC CTG CGA TCC CGT ACC CAT       192
Glu Ser Ile Arg Asp Ala His Phe Ile Gly Leu Arg Ser Arg Thr His
 50                  55                  60

CTG ACT GAA GAC GTG ATC AAC GCC GCA GAA AAA CTG GTC GCT ATT GGC       240
Leu Thr Glu Asp Val Ile Asn Ala Ala Glu Lys Leu Val Ala Ile Gly
 65                  70                  75                  80

TGT TTC TGT ATC GGA ACA AAC CAG GTT GAT CTG GAT GCG GCG GCA AAG       288
Cys Phe Cys Ile Gly Thr Asn Gln Val Asp Leu Asp Ala Ala Ala Lys
             85                  90                  95

CGC GGG ATC CCG GTA TTT AAC GCA CCG TTC TCA AAT ACG CGC TCT GTT       336
Arg Gly Ile Pro Val Phe Asn Ala Pro Phe Ser Asn Thr Arg Ser Val
            100                 105                 110

GCG GAG CTG GTG ATT GGC GAA CTG CTG CTG CTA TTG CGC GGC GTG CCG       384
Ala Glu Leu Val Ile Gly Glu Leu Leu Leu Leu Leu Arg Gly Val Pro
        115                 120                 125

GAA GCC AAT GCT AAA GCG CAC CGT GGC GTG TGG AAC AAA CTG GCG GCG       432
Glu Ala Asn Ala Lys Ala His Arg Gly Val Trp Asn Lys Leu Ala Ala
        130                 135                 140

GGT TCT TTT GAA GCG CGC GGC AAA AAG CTG GGT ATC ATC GGC TAC GGT       480
Gly Ser Phe Glu Ala Arg Gly Lys Lys Leu Gly Ile Ile Gly Tyr Gly
145                 150                 155                 160

CAT ATT GGT ACG CAA TTG GGC ATT CTG GCT GAA TCG CTG GGA ATG TAT       528
His Ile Gly Thr Gln Leu Gly Ile Leu Ala Glu Ser Leu Gly Met Tyr
                165                 170                 175

GTT TAC TTT TAT GAT ATT GAA AAT AAA CTG CCG CTG GGC AAC GCC ACT       576
Val Tyr Phe Tyr Asp Ile Glu Asn Lys Leu Pro Leu Gly Asn Ala Thr
            180                 185                 190

CAG GTA CAG CAT CTT TCT GAC CTG CTG AAT ATG AGC GAT GTG GTG AGT       624
Gln Val Gln His Leu Ser Asp Leu Leu Asn Met Ser Asp Val Val Ser
        195                 200                 205

CTG CAT GTA CCA GAG AAT CCG TCC ACC AAA AAT ATG ATG GGC GCG AAA       672
Leu His Val Pro Glu Asn Pro Ser Thr Lys Asn Met Met Gly Ala Lys
    210                 215                 220

GAA ATT TCA CTA ATG AAG CCC GGC TCG CTG CTG ATT AAT GCT TCG CGC       720
Glu Ile Ser Leu Met Lys Pro Gly Ser Leu Leu Ile Asn Ala Ser Arg
225                 230                 235                 240

GGT ACT GTG GTG GAT ATT CCG GCG CTG TGT GAT GCG CTG GCG AGC AAA       768
Gly Thr Val Val Asp Ile Pro Ala Leu Cys Asp Ala Leu Ala Ser Lys
                245                 250                 255

CAT CTG GCG GGG GCG GCA ATC GAC GTA TTC CCG ACG GAA CCG GCG ACC       816
His Leu Ala Gly Ala Ala Ile Asp Val Phe Pro Thr Glu Pro Ala Thr
            260                 265                 270

AAT AGC GAT CCA TTT ACC TCT CCG CTG TGT GAA TTC GAC AAC GTC CTT       864
Asn Ser Asp Pro Phe Thr Ser Pro Leu Cys Glu Phe Asp Asn Val Leu
        275                 280                 285

CTG ACG CCA CAC ATT GGC GGT TCG ACT CAG GAA GCG CAG GAG AAT ATC       912
```

| | | | | | | | | | | | | | | | | |
|---|---|---|---|---|---|---|---|---|---|---|---|---|---|---|---|---|
| Leu | Thr | Pro | His | Ile | Gly | Gly | Ser | Thr | Gln | Glu | Ala | Gln | Glu | Asn | Ile | |
| | 290 | | | | 295 | | | | | 300 | | | | | | |
| GGC | CTG | GAA | GTT | GCG | GGT | AAA | TTG | ATC | AAG | TAT | TCT | GAC | AAT | GGC | TCA | 960 |
| Gly | Leu | Glu | Val | Ala | Gly | Lys | Leu | Ile | Lys | Tyr | Ser | Asp | Asn | Gly | Ser | |
| 305 | | | | | 310 | | | | | 315 | | | | | 320 | |
| ACG | CTC | TCT | GCG | GTG | AAC | TTC | CCG | GAA | GTC | TCG | CTG | CCA | CTG | CAC | GGT | 1008 |
| Thr | Leu | Ser | Ala | Val | Asn | Phe | Pro | Glu | Val | Ser | Leu | Pro | Leu | His | Gly | |
| | | | | 325 | | | | | 330 | | | | | 335 | | |
| GGG | CGT | CGT | CTG | ATG | CAC | ATC | CAC | GAA | AAC | CGT | CCG | GGC | GTG | CTA | ACT | 1056 |
| Gly | Arg | Arg | Leu | Met | His | Ile | His | Glu | Asn | Arg | Pro | Gly | Val | Leu | Thr | |
| | | | 340 | | | | | 345 | | | | | 350 | | | |
| GCG | CTG | AAC | AAA | ATC | TTC | GCC | GAG | CAG | GGC | GTC | AAC | ATC | GCC | GCG | CAA | 1104 |
| Ala | Leu | Asn | Lys | Ile | Phe | Ala | Glu | Gln | Gly | Val | Asn | Ile | Ala | Ala | Gln | |
| | | 355 | | | | | 360 | | | | | 365 | | | | |
| TAT | CTG | CAA | ACT | TCC | GCC | CAG | ATG | GGT | TAT | GTG | GTT | ATT | GAT | ATT | GAA | 1152 |
| Tyr | Leu | Gln | Thr | Ser | Ala | Gln | Met | Gly | Tyr | Val | Val | Ile | Asp | Ile | Glu | |
| | 370 | | | | | 375 | | | | | 380 | | | | | |
| GCC | GAC | GAA | GAC | GTT | GCC | GAA | AAA | GCG | CTG | CAG | GCA | ATG | AAA | GCT | ATT | 1200 |
| Ala | Asp | Glu | Asp | Val | Ala | Glu | Lys | Ala | Leu | Gln | Ala | Met | Lys | Ala | Ile | |
| 385 | | | | | 390 | | | | | 395 | | | | | 400 | |
| CCG | GGT | ACC | ATT | CGC | GCC | CGT | CTG | CTG | TAC | TAA | | | | | | 1233 |
| Pro | Gly | Thr | Ile | Arg | Ala | Arg | Leu | Leu | Tyr | End | | | | | | |
| | | | | 405 | | | | | 410 | | | | | | | |

( 2 ) INFORMATION FOR SEQ ID NO:2:

( i ) SEQUENCE CHARACTERISTICS:
        ( A ) LENGTH: 52 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:2:

| | | | | | | | | | | | | | | |
|---|---|---|---|---|---|---|---|---|---|---|---|---|---|---|
| Ala | Glu | Gln | Gly | Val | Asn | Ile | Ala | Ala | Gln | Tyr | Leu | Gln | Thr | Ser | Ala |
| 1 | | | | 5 | | | | | 10 | | | | | 15 | |
| Gln | Met | Gly | Tyr | Val | Val | Ile | Asp | Ile | Glu | Ala | Asp | Glu | Asp | Val | Ala |
| | | | 20 | | | | 25 | | | | | 30 | | | |
| Glu | Lys | Ala | Leu | Gln | Ala | Met | Lys | Ala | Ile | Pro | Gly | Thr | Ile | Arg | Ala |
| | | 35 | | | | 40 | | | | | 45 | | | | |
| Arg | Leu | Leu | Tyr | | | | | | | | | | | | |
| | 50 | | | | | | | | | | | | | | |

( 2 ) INFORMATION FOR SEQ ID NO:3:

( i ) SEQUENCE CHARACTERISTICS:
        ( A ) LENGTH: 47 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:3:

| | | | | | | | | | | | | | | | |
|---|---|---|---|---|---|---|---|---|---|---|---|---|---|---|---|
| Ala | Glu | Gln | Gly | Val | Asn | Ile | Ala | Ala | Gln | Tyr | Leu | Gln | Thr | Ser | Ala |
| 1 | | | | 5 | | | | | 10 | | | | | 15 | |
| Gln | Met | Gly | Tyr | Val | Val | Ile | Asp | Ile | Glu | Ala | Asp | Glu | Asp | Val | Ala |
| | | | 20 | | | | 25 | | | | | 30 | | | |
| Glu | Lys | Ala | Leu | Gln | Ala | Met | Lys | Ala | Ile | Pro | Ala | Ser | Leu | Asp | |
| | | 35 | | | | 40 | | | | | 45 | | | | |

( 2 ) INFORMATION FOR SEQ ID NO:4:

( i ) SEQUENCE CHARACTERISTICS:

(A) LENGTH: 7 amino acids
(B) TYPE: amino acid
(D) TOPOLOGY: linear (ii) MOLECULE TYPE: peptide (xi) SEQUENCE DESCRIPTION: SEQ ID NO:4:

Ala Glu Gln Gly Val Leu Val
1               5

(2) INFORMATION FOR SEQ ID NO:5:

(i) SEQUENCE CHARACTERISTICS:
(A) LENGTH: 6 amino acids
(B) TYPE: amino acid
(D) TOPOLOGY: linear (ii) MOLECULE TYPE: peptide (xi) SEQUENCE DESCRIPTION: SEQ ID NO:5:

Ala Glu Gln Gly Val Leu
1               5

(2) INFORMATION FOR SEQ ID NO:6:

(i) SEQUENCE CHARACTERISTICS:
(A) LENGTH: 56 amino acids
(B) TYPE: amino acid
(D) TOPOLOGY: linear (ii) MOLECULE TYPE: peptide (xi) SEQUENCE DESCRIPTION: SEQ ID NO:6:

Ala Glu Gln Gly Val Cys Ser Arg Ala Asn Ile Ala Ala Gln Tyr Leu
1               5                   10                  15

Gln Thr Ser Ala Gln Met Gly Tyr Val Val Ile Asp Ile Glu Ala Asp
            20                  25                  30

Glu Asp Val Ala Glu Lys Ala Leu Gln Ala Met Lys Ala Ile Pro Gly
            35                  40                  45

Thr Ile Arg Ala Arg Leu Leu Tyr
    50                  55

(2) INFORMATION FOR SEQ ID NO:7:

(i) SEQUENCE CHARACTERISTICS:
(A) LENGTH: 54 amino acids
(B) TYPE: amino acid
(D) TOPOLOGY: linear (ii) MOLECULE TYPE: peptide (xi) SEQUENCE DESCRIPTION: SEQ ID NO:7:

Ala Glu Gln Gly Val Asn Ile Ala Ala Gln Tyr Leu Gln Thr Ser Ala
1               5                   10                  15

Gln Met Gly Tyr Val Val Ile Asp Ile Glu Ala Asp Glu Asp Val Ala
            20                  25                  30

Glu Lys Ala Leu Ser Arg Gln Ala Met Lys Ala Ile Pro Gly Thr Ile
            35                  40                  45

Arg Ala Arg Leu Leu Tyr
    50

(2) INFORMATION FOR SEQ ID NO:8:

(i) SEQUENCE CHARACTERISTICS:
(A) LENGTH: 37 amino acids
(B) TYPE: amino acid (D) TOPOLOGY: linear (ii) MOLECULE TYPE: peptide (xi) SEQUENCE DESCRIPTION: SEQ ID NO:8:

```
Ala Glu Gln Gly Val Asn Ile Ala Ala Gln Tyr Leu Gln Thr Ser Ala
 1               5                  10                      15
Gln Met Gly Tyr Val Val Ile Asp Ile Glu Ala Asp Glu Asp Val Ala
                20                  25                  30
Glu Lys Ala Leu Leu
            35
```

(2) INFORMATION FOR SEQ ID NO:9:

(i) SEQUENCE CHARACTERISTICS:
(A) LENGTH: 53 amino acids
(B) TYPE: amino acid
(D) TOPOLOGY: linear (ii) MOLECULE TYPE: peptide (xi) SEQUENCE DESCRIPTION: SEQ ID NO:9:

```
Ala Glu Gln Gly Val Asn Ile Ala Ala Gln Tyr Leu Gln Thr Ser Ala
 1               5                  10                      15
Gln Met Gly Tyr Val Val Ile Asp Ile Glu Ala Asp Glu Asp Val Ala
                20                  25                  30
Glu Lys Ala Leu Gln Ala Met Lys Ala Ile Pro Gly Thr Ala Ile Arg
            35                  40                  45
Ala Arg Leu Leu Tyr
        50
```

(2) INFORMATION FOR SEQ ID NO:10:

(i) SEQUENCE CHARACTERISTICS:
(A) LENGTH: 45 amino acids
(B) TYPE: amino acid
(D) TOPOLOGY: linear (ii) MOLECULE TYPE: peptide (xi) SEQUENCE DESCRIPTION: SEQ ID NO:10:

```
Ala Glu Gln Gly Val Asn Ile Ala Ala Gln Tyr Leu Gln Thr Ser Ala
 1               5                  10                      15
Gln Met Gly Tyr Val Val Ile Asp Ile Glu Ala Asp Glu Asp Val Ala
                20                  25                  30
Glu Lys Ala Leu Gln Ala Met Lys Ala Ile Pro Val Leu
            35                  40              45
```

(2) INFORMATION FOR SEQ ID NO:11:

(i) SEQUENCE CHARACTERISTICS:
(A) LENGTH: 16 amino acids
(B) TYPE: amino acid
(D) TOPOLOGY: linear (ii) MOLECULE TYPE: peptide (xi) SEQUENCE DESCRIPTION: SEQ ID NO:11:

```
Ala Glu Gln Gly Val Cys Ser Arg Ala Ile Arg Ala Arg Leu Leu Tyr
 1               5                  10                      15
```

(2) INFORMATION FOR SEQ ID NO:12:

(i) SEQUENCE CHARACTERISTICS:
(A) LENGTH: 46 amino acids (B) TYPE: amino acid
            (D) TOPOLOGY: linear (ii) MOLECULE TYPE: peptide (xi) SEQUENCE DESCRIPTION: SEQ ID NO:12:

Ala Glu Gln Gly Val Asn Ile Ala Ala Gln Tyr Leu Gln Thr Ser Ala
1               5                   10                  15

Gln Met Gly Tyr Val Val Ile Asp Ile Glu Ala Asp Glu Asp Val Ala
            20                  25                  30

Glu Lys Ala Leu Ser Arg Ala Ile Arg Ala Arg Leu Leu Tyr
            35                  40                  45

(2) INFORMATION FOR SEQ ID NO:13:

(i) SEQUENCE CHARACTERISTICS:
            (A) LENGTH: 14 base pairs
            (B) TYPE: nucleic acid
            (C) STRANDEDNESS: double
            (D) TOPOLOGY: linear (ii) MOLECULE TYPE: DNA (xi) SEQUENCE DESCRIPTION: SEQ ID NO:13:

CTAGTCTAGA CTAG                                                                14

(2) INFORMATION FOR SEQ ID NO:14:

(i) SEQUENCE CHARACTERISTICS:
            (A) LENGTH: 8 base pairs
            (B) TYPE: neucleic acid
            (C) STRANDEDNESS: double
            (D) TOPOLOGY: linear (ii) MOLECULE TYPE: DNA (xi) SEQUENCE DESCRIPTION: SEQ ID NO:14:

CTCTAGAG                                                                        8

(2) INFORMATION FOR SEQ ID NO:15:

(i) SEQUENCE CHARACTERISTICS:
            (A) LENGTH: 12 base pairs
            (B) TYPE: nucleic acid
            (C) STRANDEDNESS: double
            (D) TOPOLOGY: linear (ii) MOLECULE TYPE: DNA (xi) SEQUENCE DESCRIPTION: SEQ ID NO:15:

TGCTCTAGAG CA                                                                  12

(2) INFORMATION FOR SEQ ID NO:16:

(i) SEQUENCE CHARACTERISTICS:
            (A) LENGTH: 10 base pairs
            (B) TYPE: nucleic acid
            (C) STRANDEDNESS: double
            (D) TOPOLOGY: linear (ii) MOLECULE TYPE: DNA (xi) SEQUENCE DESCRIPTION: SEQ ID NO:16:

GCTCTAGAGC                                                                     10

(2) INFORMATION FOR SEQ ID NO:17:

(i) SEQUENCE CHARACTERISTICS:

(A) LENGTH: 11 base pairs
(B) TYPE: nucleic acid
(C) STRANDEDNESS: double
(D) TOPOLOGY: linear (ii) MOLECULE TYPE: DNA (xi) SEQUENCE DESCRIPTION: SEQ ID NO:17:

GCTCTAGAGC A    11

(2) INFORMATION FOR SEQ ID NO:18:

(i) SEQUENCE CHARACTERISTICS:
(A) LENGTH: 11 base pairs
(B) TYPE: nucleic acid
(C) STRANDEDNESS: double
(D) TOPOLOGY: linear (ii) MOLECULE TYPE: DNA (xi) SEQUENCE DESCRIPTION: SEQ ID NO:18:

TGCTCTAGAG C    11